United States Patent [19]
Davis et al.

[11] Patent Number: 5,665,378
[45] Date of Patent: Sep. 9, 1997

[54] TRANSDERMAL THERAPEUTIC FORMULATION

[76] Inventors: Roosevelt Davis; Susan A. Primo-Davis, both of 27 Lullwater Estate Rd., Atlanta, Ga. 30307

[21] Appl. No.: 560,806

[22] Filed: Nov. 21, 1995

Related U.S. Application Data

[63] Continuation-in-part of Ser. No. 315,343, Sep. 30, 1994, abandoned.

[51] Int. Cl.$^6$ ...................................................... A61F 13/00
[52] U.S. Cl. .......................... 424/448; 424/447; 514/899; 514/947; 514/953
[58] Field of Search ...................... 424/447–449; 514/899, 947, 953

[56] References Cited

U.S. PATENT DOCUMENTS

| | | | |
|---|---|---|---|
| 4,313,958 | 2/1982 | Lahann | 424/324 |
| 4,346,709 | 8/1982 | Schmitt | 128/260 |
| 4,440,777 | 4/1984 | Zupan | 424/274 |
| 4,575,515 | 3/1986 | Sandborn | 514/708 |
| 4,681,897 | 7/1987 | Brand | 514/557 |
| 4,738,670 | 4/1988 | Von Bittera | 604/306 |
| 4,746,509 | 5/1988 | Haggiage et al. | 424/449 |
| 4,931,283 | 6/1990 | Tsuk | 424/449 |
| 4,997,853 | 3/1991 | Bernstein | 514/626 |
| 4,999,379 | 3/1991 | Fankhauser | 514/567 |
| 5,155,105 | 10/1992 | Jones | 514/223.5 |
| 5,164,416 | 11/1992 | Nagai et al. | 514/763 |
| 5,296,225 | 3/1994 | Adekunle | 424/195.1 |
| 5,318,960 | 6/1994 | Toppo | 514/159 |

OTHER PUBLICATIONS

Griffin et al., Nonsteroidal Anti–inflammatory Drug Use and Increased Risk for Peptic Ulcer Disease in Elderly Persons, Reprinted from *Annals of Internal Medicine* vol. 114; No. 4; 15 Feb. 1991.

Bradley et al., Comparison of an Antiinflammatory Dose of Ibuprofen, An Analgesic Dose of Ibuprofen, and Acetaminophen in the Treatment of Patients with Osteoarthritis of the Knee, Reprinted from *The New England Journal of Medicine*, 325:87–91 Jul. 11, 1991.

*Primary Examiner*—D. Gabrielle Phelan
*Attorney, Agent, or Firm*—Connolly & Hutz

[57] ABSTRACT

The present invention relates to a transdermal therapeutic formulation comprising capsaicin, a nonsteroidal anti-inflammatant and pamabrom. The formulation is used to alleviate pain or discomfort in a mammal by being applied to the skin of the mammal thereby causing the active ingredients in the formulation to pass into and/or through the skin of the mammal. In a preferred embodiment of the present invention, the formulation is used in patch form for the treatment of the pain and discomfort associated with menstrual cramps, water retention (e.g., "bloating") and/or muscular pain (e.g., muscular back pain).

19 Claims, 1 Drawing Sheet

TRANSDERMAL THERAPEUTIC FORMULATION

CROSS-REFERENCE TO RELATED APPLICATION

This application is a continuation-in-part of U.S. patent application Ser. No. 08/315,343 which was filed on Sep. 30, 1994, now abandoned in the names of Roosevelt Davis et al.

BRIEF DESCRIPTION OF THE INVENTION

The present invention relates to a transdermal therapeutic formulation comprising capsaicin, a nonsteroidal anti-inflammatant and pamabrom. In a preferred embodiment of the present invention, the formulation is used in patch form for the treatment of menstrual cramps and/or muscular back pain.

BACKGROUND OF THE INVENTION

In general, analgesics fall into two broad categories. The simple analgesics, such as aspirin, are most effective against pain of integumental origin, headache, and muscle ache; the narcotics are more useful for deep or visceral pain. Narcotic analgesics such as morphine produce more profound effects than simple analgesics, and are potentially addicting, with the development of tolerance and physical dependence. The morphine-like analgesics appear to work through interaction with the endorphin/enkephalin system of the central nervous system; many, if not all of the simple, non-narcotic analgesics appear to work by inhibition of prostaglandin synthetase. The effect of narcotics is to elevate the pain threshold above the normal level; the non-narcotic analgesics act to raise an abnormally low pain threshold to the normal level. The narcotic analgesics are antagonized by compounds such as naloxone; the non-narcotic analgesics are not.

Capsaicin (8-methyl-N-vanillyl-6-nonenamide), which is the pungent component of paprika, is a potent analgesic. However, it appears to be largely unrelated to the two known classes of analgesics. In certain tests, it produces a level of analgesia comparable to morphine, yet it is not antagonized by classical narcotic antagonists, such as naloxone. It effectively prevents the development of cutaneous hyperalgesia, but appears to have minimal effects on normal pain responses at moderate doses. At high doses capsaicin also exerts analgesic activity in classical models of deep pain, elevating the pain threshold above the normal value.

Capsaicin has the following structure:

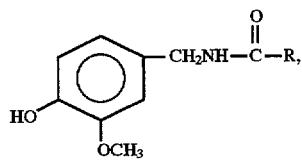

where R is —$(CH_2)_4CH=CH—CH(CH_3)_2$

Capsaicin can be readily obtained by the ethanol extraction of the fruit of capsicum frutescens or capsicum annum. It is available commercially from a variety of suppliers, and can also be prepared synthetically by published methods. In some commercially available forms of capsaicin, R=—$(CH_2)_7C_3$. This "pseudocapsaicin" is pharmacologically indistinguishable from natural capsaicin. The present invention encompasses the use of both forms, and where the term "capsaicin" is used, both forms are meant.

Nonsteroidal anti-inflammatory drugs (NSAIDS) generally have a low pH and can be corrosive to portions of the gastrointestinal tract, especially the stomach lining. Recent research has shown that these drugs, when taken orally, can increase the patients' risk for developing peptic ulcer disease and upper gastrointestinal bleeding, especially in elderly persons. The detrimental effects of these drugs on the gastrointestinal tract increase as the dose of the NSAID increases. Therefore, there is a need for a method of delivering these drugs to the body that can bypass the gastrointestinal tract and provide effective relief at lower doses.

The main reason why relatively large doses of NSAIDS must be used when the drugs are taken orally is that the drugs are very effectively metabolized in the liver before they can be delivered to the circulation system of the patient, (i.e., the so-called "first pass" metabolism). For example, first pass metabolism can decrease the amount of drug that reaches the site of action by about 30 to 70 percent depending on the chemical make-up of the drug. Since the efficacy of pharmaceutical products in general depends not only on the amount of the active ingredient that enters the circulatory system but also on the amount of active ingredient that reaches the receptor site or site of action, it should be apparent that any method of providing the active ingredient to the body which bypasses the liver and/or stomach would be very desirable and could also result in more rapid and predictable effects with a given dosage. Accordingly, an effective transdermal delivery system for NSAIDS would be very desirable, especially for treating pain and discomfort associated with the muscles or joints of a mammal.

Pamabrom is an 8-Bromotheophylline compound with 2-amino-2-methyl-1-propanol (1:1) which is used as a diuretic agent. The chemical structure of pamabrom is set forth below.

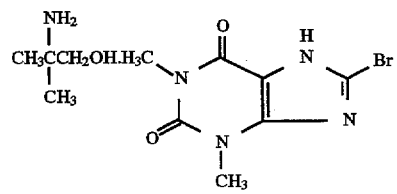

The term nonsteroidal anti-inflammatory drugs (NSAIDS), as used herein, includes, but is not necessarily limited to, the following substances: diflunisal; fenoprofen; ibuprofen; indomethacin; meclofenamate; naproxen; oxyphenbutazone; phenylbutazone; piroxicam; sulindac; tolmetin; salicylates and zomepirac.

The term "pharmaceutically-acceptable carrier" as used herein means a pharmaceutically acceptable material, composition or vehicle, such as a liquid or solid filler, diluent, excipient, or solvent involved in carrying or transporting a chemical agent from one organ or portion of the body to another organ or portion of the body.

The term "transdermal delivery" as used herein means administration of the pharmaceutical composition topically to the skin wherein the active ingredient will be percutaneously delivered in a therapeutically effective amount.

The term "transdermal patch" as used herein means a skin patch to be applied to the mammals skin containing the pharmaceutical composition. The technology for constructing transdermal patches is well known in the pharmaceutical art.

The terms "backing layer" and "reservoir" as used herein are components of the transdermal patch. Suitable materials and designs are well known in the transdermal drug delivery art. See for example D. Hsien, "Multiple Lamination for Transdermal Patches," *Controlled Release Systems Fabrication Technology*, Vol. 1, pp. 167–188. 1988.

Eucalyptol is a well-known chemical compound which has long been used as an inhalational expectorant. It is also known by the names cineole and cajeputol. The art is also well-versed in the preparation of eucalyptol.

Menthol is a secondary alcohol obtained naturally from peppermint or other mint oils or prepared synthetically. Menthol has many uses as an ingredient in various medicinal preparations due to its analgesic, local anesthetic and counter irritant properties. It is known in the pharmaceutical art that menthol acts to enhance the percutaneous transfer of systemically active drugs in mammals.

SUMMARY OF THE INVENTION

The present invention relates to a transdermal therapeutic formulation comprising capsaicin, a nonsteroidal anti-inflammatant and pamabrom. The formulation is used to alleviate pain or discomfort in a mammal by being applied to the skin of the mammal thereby causing the active ingredients in the formulation to pass into and/or through the skin of the mammal. In a preferred embodiment of the present invention, the formulation is used in patch form for the treatment of menstrual cramps and/or muscular back pain.

The formulation of the present invention can also contain additional substances such as, for example, skin permeation enhancers. In a preferred embodiment of the present invention, the formulation includes menthol, eucalyptol and/or glyceryl monostearate in an amount which is sufficient to enhance skin permeation of one or more of the other substances contained in the formulation. In another preferred embodiment of the present invention, the formulation includes d-limonene, either by itself or in addition to the menthol, eucalyptol and/or glyceryl monostearate.

The active ingredients of the formulation of the present invention will be carried by or within a pharmaceutically-acceptable carrier. The formulation will be used by applying it to the skin of a mammal for a time which is sufficient to allow a portion of the active ingredients to pass into and/or through the skin. The portion that passes into and/or through the skin must be sufficient to have the desired therapeutic effect, for example the alleviation of pain or the soothing of muscular cramps. Therefore, the amount of the formulation that is applied to the skin must be sufficient to achieve the desired therapeutic effect. The factors which will influence the amount of formulation that is necessary to achieve the desired therapeutic effect include the following: (1) the concentration of the active ingredients in the formulation; (2) the effectiveness of the skin permeation enhancers; (3) the location on the body of the mammal that the application of the formulation occurs in relation to the source of the pain or discomfort; and (4) the size and skin thickness (or toughness) of the mammal.

Although the formulation may be applied to the skin through the use of any form of transdermal delivery system (e.g., creams, lotions, patches, tapes, polymeric systems such as erodible polymers or film-forming polymers which contain the formulation, etc.), the preferred method of delivery is through the use of a transdermal patch which contains the formulation and releases it over time onto the skin of the mammal at a desired location. The technology for constructing transdermal patches is well known in the art and any of the known patch designs would be suitable for the transdermal delivery of the formulations of the present invention. Generally, referring to FIG. 1, the patch 10 will contain: (1) a backing layer 12; (2) a reservoir 18; (3) an adhesive layer 16 and (4) a protective undercoating 19. Before use, the protective undercoating is removed from the patch so that the reservoir and adhesive layer can be contacted with the skin of the mammal. The reservoir is constructed so that it can contain an amount of the formulation which is sufficient to continuously provide the active ingredients to the surface of the skin for a predetermined period of time. After the active ingredients have been depleted from the reservoir, the patch is removed from the skin and discarded or, if appropriate, reapplied after the reservoir has been replenished with the formulation.

DETAILED DESCRIPTION OF THE INVENTION

Figure 1:
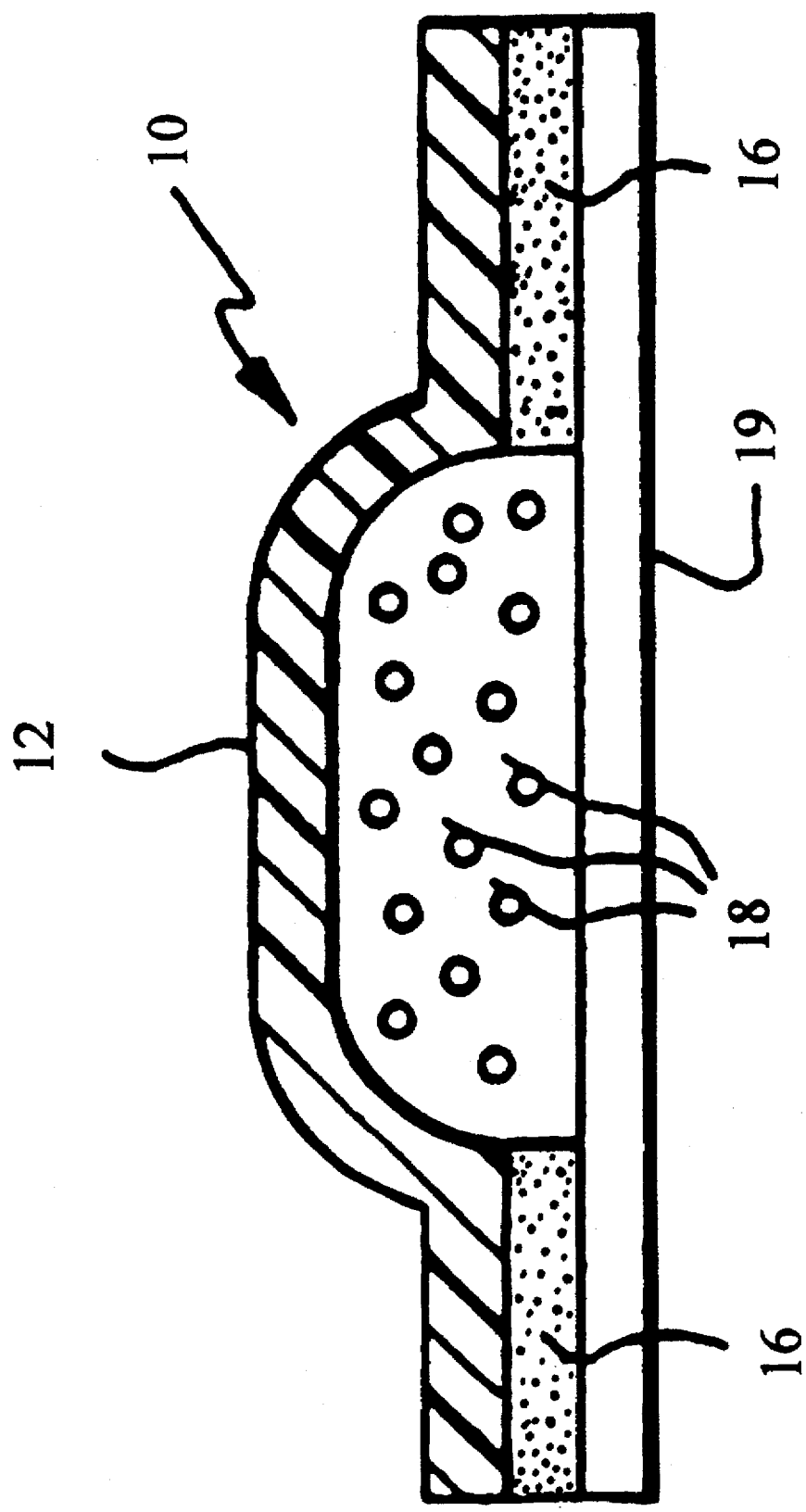
FIG. 1 is a cross-sectional view of a transdermal patch that is designed to be placed on the skin of a mammal for transdermal delivery of the active ingredients of the formulation of the present invention.

The present invention relates to a transdermal therapeutic formulation comprising capsaicin, a nonsteroidal anti-inflammatant and pamabrom. The formulation is used to alleviate pain or discomfort in a mammal by being applied to the skin of the mammal thereby causing the active ingredients in the formulation to pass into and/or through the skin of the mammal. In a preferred embodiment of the present invention, the formulation is used in patch form for the treatment of menstrual cramps and/or muscular back pain.

The formulation of the present invention can also contain additional substances such as, for example, skin permeation enhancers. In a preferred embodiment of the present invention, the formulation includes menthol, eucalyptol and/or glyceryl monostearate in an amount which is sufficient to enhance skin permeation of one or more of the other substances contained in the formulation. In another preferred embodiment of the present invention, the formulation includes d-limonene, either by itself or in addition to the menthol, eucalyptol and/or glyceryl monostearate.

The formulation of the present invention can also contain antihistamines, such as pyrilamine maleate.

The active ingredients of the formulation of the present invention will be carried by or within a pharmaceutically-acceptable carrier. The formulation will be used by applying it to the skin of a mammal for a time which is sufficient to allow a portion of the active ingredients to pass into and/or through the skin. The portion that passes into and/or through the skin must be sufficient to have the desired therapeutic effect, for example the alleviation of pain or the soothing of muscular cramps. Therefore, the amount of the formulation that is applied to the skin must be sufficient to achieve the desired therapeutic effect. The factors which will influence the amount of formulation that is necessary to achieve the desired therapeutic effect include the following: (1) the concentration of the active ingredients in the formulation; (2) the effectiveness of the skin permeation enhancers; (3) the location on the body of the mammal that the application of the formulation occurs in relation to the source of the pain or discomfort; and (4) the size and skin thickness (or toughness) of the mammal.

Although the formulation may be applied to the skin through the use of any form of transdermal delivery system (e.g., creams, lotions, patches, tapes, polymeric systems such as erodible polymers or film-forming polymers which contain the formulation, etc.), the preferred method of delivery is through the use of a transdermal patch which contains the formulation and releases it over time onto the skin of the mammal at a desired location. The technology for constructing transdermal patches is well known in the art and any of the known patch designs would be suitable for the transdermal delivery of the formulations of the present invention. Generally, referring to FIG. 1, the patch 10 will contain: (1) a backing layer 12; (2) a reservoir 18; (3) an adhesive layer 16 and (4) a protective undercoating 19. Before use, the protective undercoating is removed from the patch so that the reservoir and adhesive layer can be contacted with the skin of the mammal. The reservoir is constructed so that it can contain an amount of the formulation which is sufficient to continuously provide the active ingredients to the surface of the skin for a predetermined period of time. Any type of reservoir means can be used in the patch of the present invention. For example, the reservoir means may take various forms such as pads or sponges impregnated with the active ingredients, a polymeric matrix containing the active ingredients, a gel formulation (or other formulation having some structural integrity) of the active ingredients, a composition or solution of the active ingredients within a walled container permeable to the active ingredients and available to the skin or membrane of the mammal, a multiplicity of distinct microreservoir compartments each containing at least one of the active ingredients, layers of reservoirs containing at least one of the active ingredients and multiple variants of any of these reservoir examples. After the active ingredients have been depleted from the reservoir, the patch is removed from the skin and discarded or, if appropriate, reapplied after the reservoir has been replenished with the formulation.

The primary ingredients in the formulation of the present invention are capsaicin, a non-steroidal anti-inflammatant and pamabrom. In a preferred embodiment of the present invention, the formulation also contains at least one skin permeation enhancer in an amount which is sufficient to enhance skin permeation of one or more of the other primary ingredients of the formulation. Preferred skin permeation enhancers for use in the formulation of the present invention include menthol and/or eucalyptol and/or d-limonene and/or glyceryl monostearate.

The relative amounts of the primary ingredients in the formulation will depend on the effect that is desired by use of the formulation. For example, if the formulation is to be used to treat pain that is not accompanied by muscular discomfort (such as cramps), the amount of nonsteroidal anti-inflammatant that is contained in the formulation should be increased relative to the amount of capsaicin and pamabrom. However, if the primary effect that is desired is the alleviation of muscular discomfort, the amount of capsaicin should be increased relative to the amount of nonsteroidal anti-inflammatant and pamabrom. Moreover, when the discomfort is at least partially caused by the retention of water in any part of the body, the amount of pamabrom that is used should be sufficient to reduce the water retention and thereby alleviate the discomfort. When the effect that is desired to be achieved is the overall alleviation of both pain and discomfort (e.g., both muscular discomfort and discomfort that is related to water rententiom), a sufficient amount of capsaicin, nonsteroidal anti-inflammatant and pamabrom should be present in the formulation.

In a preferred embodiment of the present invention, the formulation is used to alleviate the pain and discomfort caused by menstrual cramps and water retention (e.g., "bloating"). In this embodiment, the formulation would be applied to the skin in an area that is closest to the portion of the body that is experiencing the most discomfort, for example, the lower abdomen or inguinal region. When the formulation is contained within a patch, the patch would be applied to the skin, for example, on a convenient portion of the lower abdomen or inguinal region. Formulations containing varying concentrations of the active ingredients could be prepared to treat the different levels of discomfort that are experienced by each individual.

In another preferred embodiment of the present invention, the formulation is used to alleviate the pain and discomfort associated with muscular pain, especially muscular back pain. In this embodiment, the formulation would be applied to the skin in an area that is closest to the portion of the body that is experiencing the most discomfort, for example, the lower back. When the formulation is contained within a patch, the patch would be applied to the skin, for example, on a convenient portion of the lower back. Formulations containing varying concentrations of the active ingredients could be prepared to treat the different levels of discomfort that are experienced by each individual.

The nonsteroidal anti-inflammatant that is used in the formulation of the present invention may be any such substance that is compatible with capsaicin and pamabrom (i.e., does not react unfavorably with capsaicin and/or pamabrom so as to significantly reduce the effectiveness of the capsaicin and/or pamabrom). Preferred non-steroidal anti-inflammatants include ibuprofen, naproxen, diclofenac sodium and mixtures thereof.

The composition of the present invention will usually contain from about 0.001–5% (preferably 0.005–5%) by weight capsaicin, from about 0.5–40% by weight of at least one nonsteroidal anti-inflammatant, from about 0.001–5% (preferably 0.005–5%) by weight of pamabrom, from about 15–40% by weight of at least one skin permeation enhancer and from about 10–84.5% by weight of a pharmaceutically acceptable carrier.

The following examples are intended to illustrate several preferred embodiments of the present invention. The examples should not be interpreted as limiting the scope of the present invention to the specific embodiments described therein.

EXAMPLE 1

A transdermal patch containing the ingredients listed in Table 1 can be prepared as described below.

TABLE 1

| | |
|---|---|
| nonsteroidal anti-inflammatory agent (ibuprofen) | 1 g |
| capsaicin | 1 g |
| pamabrom | 0.5 g |
| d-limonene | 15 g |
| glycerin | 20 g |
| polyacrylate copolymer | 1 g |
| eucalyptol | 10 g |
| polyvinyl alcohol | 5 g |
| purified water | 45.5 g |
| purified gelatin | 1 g |

The polyacrylate copolymer would be dissolved in about 30 grams of purified water. Separately, the purified gelatin and polyvinyl alcohol would be dissolved in the remainder of the purified water and stirred at 60° C. for about 3 minutes. The above two solutions would then be mixed to form a first mixture. A second mixture containing the ibuprofen, capsaicin, pamabrom and the d-limonene would then be prepared and added to the first mixture to form a third mixture which would be kneaded for about 2 minutes. The glycerin would then be added to the third mixture to form a final mixture which would be kneaded for about 3 minutes. This final mixture would then be poured onto a backing layer of nonwoven fabric to form a reservoir of the final mixture. The edges of the backing layer would be coated with an adhesive substance. After the reservoir of the final mixture was established on the patch, a protective layer would be placed over the surface of the reservoir and the adhesive substance to form the final transdermal patch. The pH of the final mixture in the reservoir of the patch would be about 7.0 or would be adjusted, if necessary, to be about 7.0.

EXAMPLE 2

The following is an example of the use of a transdermal therapeutic formulation of the present invention for the treatment of abdominal pain.

A cream was prepared which contained capsaicin, a nonsteroidal anti-inflammatant (ibuprofen), pamabrom and a skin permeation enhancer (glyceryl monostearate). The cream was applied to the skin on the lower abdominal region of a human female patient at the approximate location of the maximum pain. This location was determined by the patient. The patient reported an analgesic effect in the area where the cream was applied and a mild diuretic effect.

The cream was produced by mixing together two starting creams. The first starting cream was produced by mixing 20 grams of pamabrom powder (obtained from Miles Consumer Healthcare Products, 1127 Myrtle Street, Elkhart, Ind.) and 45 grams of ibuprofen powder (obtained from Spectrum Chemical Manufacturing Co., 14422 S. San Pedro Street, Gardena, Calif.) with 130 ml of isopropyl alcohol. The second starting cream was a commercial cream containing capsaicin (i.e., Zostrix® cream which contains 0.025% by weight capsaicin in an emollient base which contains glyceryl monostearate as a skin permeation enhancer). The final cream was produced by mixing the first starting cream with 45 grams of the second starting cream.

While the invention has been particularly shown and described with reference to preferred embodiments thereof, it will be understood by those skilled in the art that various changes in form and details may be made without departing from the spirit and scope of the invention as defined in the appended claims.

What is claimed is:

1. A transdermal therapeutic formulation comprising
   a therapeutically effective amount of capsaicin;
   a therapeutically effective amount of at least one nonsteroidal anti-inflammatant;
   a therapeutically effective amount of pamabrom; and
   a premeation enhancing amount of at least one skin permeation enhancer selected from the group consisting of menthol, eucalyptol, glyceryl monostearate and d-limonene.

2. The formulation of claim 1, wherein said nonsteroidal anti-inflammatant comprises at least one substance selected from the group consisting of ibuprofen, naproxen, and diclofenac sodium.

3. A pharmaceutical composition for transdermal delivery of capsaicin, a nonsteroidal anti-inflammatant and pamabrom, said composition comprising:
   a therapeutically effective amount of capsaicin;
   a therapeutically effective amount of at least one nonsteroidal anti-inflammatant;
   a therapeutically effective amount of pamabrom;
   a permeation enhancing amount of at least one skin permeation enhancer selected from the group consisting of menthol, eucalyptol, glyceryl monostearate and d-limonene; and
   a pharmaceutically acceptable carrier.

4. The pharmaceutical composition of claim 3, wherein said nonsteroidal anti-inflammatant comprises at least one substance selected from the group consisting of ibuprofen, naproxen and diclofenac sodium.

5. The pharmaceutical composition of claim 3, wherein said composition contains from about 0.001–5% by weight capsaicin, from about 0.5–40% by weight of said at least one nonsteroidal anti-inflammatant, from about 0.001–5% by weight pamabrom, from about 15–40% by weight of said at least one skin permeation enhancer and from about 10–84.5% by weight of said pharmaceutically acceptable carrier.

6. A transdermal patch having a backing layer, a reservoir and an adhesive layer, wherein said reservoir contains the pharmaceutical composition of claim 3.

7. A method for the transdermal delivery of capsaicin, a nonsteroidal anti-inflammatant and pamabrom, said method comprising applying a formulation to the skin of a mammal, wherein said formulation comprises:
   a therapeutically effective amount of capsaicin;
   a therapeutically effective amount of at least one nonsteroidal anti-inflammatant;
   a therapeutically effective amount of pamabrom;
   a permeation enhancing amount of at least one skin permeation enhancer selected from the group consisting of menthol, eucalyptol, glyceryl monostearate and d-limonene; and
   a pharmaceutically acceptable carrier.

8. The method of claim 7, wherein said formulation is contained in the reservoir of a transdermal patch which is applied to the skin of a mammal.

9. A method of alleviating the pain and discomfort associated with menstrual cramps wherein an effective amount of the formulation of claim 1 is applied to the skin of a mammal.

10. A method of alleviating the pain and discomfort associated with menstrual cramps wherein an effective amount of the composition of claim 3 is applied to the skin of a mammal.

11. A method of alleviating the pain and discomfort associated with back pain wherein an effective amount of the formulation of claim 1 is applied to the skin of a mammal.

12. A method of alleviating the pain and discomfort associated with back pain wherein an effective amount of the composition of claim 3 is applied to the skin of a mammal.

13. The method of claim 9, wherein the formulation is applied to a portion of the skin on the lower abdomen or inguinal region of a mammal.

14. The method of claim 10, wherein the formulation is applied to a portion of the skin on the lower abdomen or inguinal region of a mammal.

15. The method of claim 11, wherein the formulation is applied to a portion of the skin on the back of a mammal.

16. The method of claim 12, wherein the formulation is applied to a portion of the skin on the back of a mammal.

17. A method of alleviating the pain and discomfort associated with menstrual cramps and water retention wherein an effective amount of the formulation of claim 1 is applied to the skin of a mammal.

18. A method of alleviating the pain and discomfort associated with menstrual cramps and water retention wherein an effective amount of the composition of claim 3 is applied to the skin of a mammal.

19. The method of claim 17, wherein the formulation is applied to a portion of the skin on the lower abdomen or inguinal region of a mammal.

* * * * *

UNITED STATES PATENT AND TRADEMARK OFFICE
CERTIFICATE OF CORRECTION

PATENT NO. : 5,665,378
DATED : September 9, 1997
INVENTOR(S) : Davis et al.

It is certified that error appears in the above-identified patent and that said Letters Patent is hereby corrected as shown below:

In Column 2, lines 35-43,

" 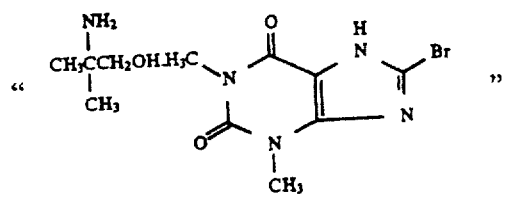 "

should be

-- 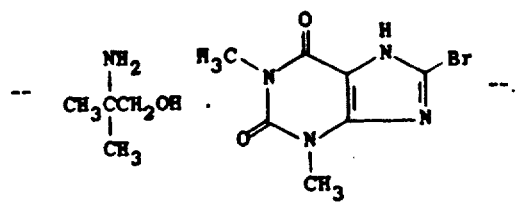 --.

In Column 7, line 48 (Claim 1), "premeation" should be --permeation--.

Signed and Sealed this

Second Day of December, 1997

Attest:

*Bruce Lehman*

BRUCE LEHMAN

*Attesting Officer*    Commissioner of Patents and Trademarks